US012797109B2

(12) United States Patent
Cronin et al.

(10) Patent No.: US 12,797,109 B2
(45) Date of Patent: Nov. 17, 2026

(54) DIRECT VISUALIZATION ENDOSCOPIC PORTAL WITH FORCE DISSIPATION

(71) Applicant: Spineology Inc., St. Paul, MN (US)

(72) Inventors: Matt Cronin, Appleton, WI (US); Saqib Hasan, San Francisco, CA (US); Sam Joseph, Tampa, FL (US); Sanjay Konakondla, Danville, PA (US); Michael Wang, Miami, FL (US); Tim Wang, Santa Ana, CA (US); Kyle Wolff, St. Paul Park, MN (US); Chris Yeung, Phoenix, AZ (US)

(73) Assignee: Spineology Inc., St. Paul, MN (US)

( * ) Notice: Subject to any disclaimer, the term of this patent is extended or adjusted under 35 U.S.C. 154(b) by 66 days.

(21) Appl. No.: 18/212,159

(22) Filed: Jun. 20, 2023

(65) Prior Publication Data

US 2023/0404618 A1 Dec. 21, 2023

Related U.S. Application Data

(60) Provisional application No. 63/353,618, filed on Jun. 19, 2022.

(51) Int. Cl.
*A61B 17/34* (2006.01)

(52) U.S. Cl.
CPC ................................ *A61B 17/3423* (2013.01)

(58) Field of Classification Search
CPC ........................ A61B 17/3421; A61B 17/3423
See application file for complete search history.

(56) References Cited

U.S. PATENT DOCUMENTS

| | | | | |
|---|---|---|---|---|
| 6,579,281 | B2 * | 6/2003 | Palmer | A61B 17/3421 606/1 |
| 10,702,257 | B2 | 7/2020 | Hess | |
| 11,241,252 | B2 | 2/2022 | Hawkins | |
| 11,529,149 | B2 | 12/2022 | Gleason | |
| 2018/0310975 | A1 * | 11/2018 | Haufe | A61B 17/848 |

* cited by examiner

*Primary Examiner* — Si Ming Ku

(57) ABSTRACT

A surgical portal or portal system can include a portal assembly and a base plate assembly. The portal assembly can include a portal head and a portal stem disposed on a distal end of the portal head. The base plate assembly can include a depth stop disposed on a force dissipating plate. The depth of a working portal can be adjusted.

12 Claims, 11 Drawing Sheets

DIRECT VISUALIZATION ENDOSCOPIC PORTAL WITH FORCE DISSIPATION

PRIORITY

This application claims the benefit of U.S. Provisional Application Ser. No. 63/353,618, filed on Jun. 19, 2022, which is hereby incorporated herein by reference in its entirety.

FIELD

The present invention generally relates to devices used in orthopedic surgeries, and more particularly to instruments, implants, tools and methods used for spinal surgical procedures such as interbody fusion procedures.

BACKGROUND

In surgical procedures it is desirable to provide instruments that allow for convenient access to the patient's anatomy for performing the procedure and for delivering implants, instruments and the like while minimizing trauma to the patient. There is a need for a surgical portal system that allows for an endoscope and surgical instruments to be passed through the same portal.

SUMMARY

The disclosure includes a low-profile force dissipation system that allows for concentric support of a working portal that is adjustable, such as up to a depth of six inches. The slotted design allows for quick insertion and removal of the plate when an end user switches to/from spinal surgical tools and instruments to an endoscope for direct visualization.

In a disclosed example, a surgical portal or portal system can comprise a portal assembly and a base plate assembly. The portal assembly can comprise a portal head and a portal stem disposed on a distal end of the portal head. The base plate assembly can comprise a depth stop disposed on a force dissipating plate.

The portal head can comprise an elongated hollow base and collar. The collar can be configured to slide longitudinally along an upper portion of the elongated hollow base. A lockout clip can be provided to the collar such that the lockout clip can slide perpendicular to a longitudinal axis of the elongated hollow base. The upper portion of the elongated hollow base can include a plurality of teeth that are arranged to be engaged by the lockout clip in a secured state. A bias member can be arranged to bias the lockout clip in the secured state. A lower portion of the elongated hollow base can define a channel to engage a proximal end of the portal stem.

The elongated hollow base can include a locking leg to secure the portal stem to the lower portion when the proximal end of the portal stem is disposed in the channel. The locking leg can be pivotally mounted on the lower portion and be biased via a spring to an engaged position.

The locking member can be removably secured to a proximal end of a hollow tubular base member. A plurality of longitudinally-spaced circumferential ribs can be defined on an outer surface thereof.

A surgical tube, cannula and/or endoscope can be disposed within the portal stem.

The depth stop can comprise a stop body and a stop release member that slides relative to the stop body. Both of the stop body and stop release member have apertures defined therethrough. The stop release member includes a channel on a proximal side of the stop body to slidably receive the stop release member. The stop release member can include grooves defined in one or more walls of the channel to engage respective projections defined on one or more sides of the stop release member to constrain the movement of the stop release member in a plane perpendicular to a longitudinal axis of the portal stem. One or more engagement grooves can be defined in one or more sidewalls of the aperture defined through the stop release member in order to engage one or more corresponding ribs on an outer surface of the tubular base member. One or more bias members can be provided to bias the stop release member in an engagement state. A pair of axles can extend horizontally from the stop body in opposite directions. A distal side of the stop body can be curved.

The force dissipation plate can comprise a plate body including a distal patient-contacting side and a proximal side. The proximal side can include a groove and a pair of fingers that extend upwards from the proximal surface. The groove and fingers can be configured such that an axle-shaped object in the groove (such as the axles of the stop body) is restrained from movement in a proximal-distal direction while permitting rotation of the axle-shaped object relative to the plate body.

The detailed technology and preferred embodiments implemented for the subject invention are described in the following paragraphs accompanying the appended drawings for people skilled in this field to well appreciate the features of the claimed invention. It is understood that the features mentioned hereinbefore and those to be commented on hereinafter may be used not only in the specified combinations, but also in other combinations or in isolation, without departing from the scope of the present invention.

Figure 1:
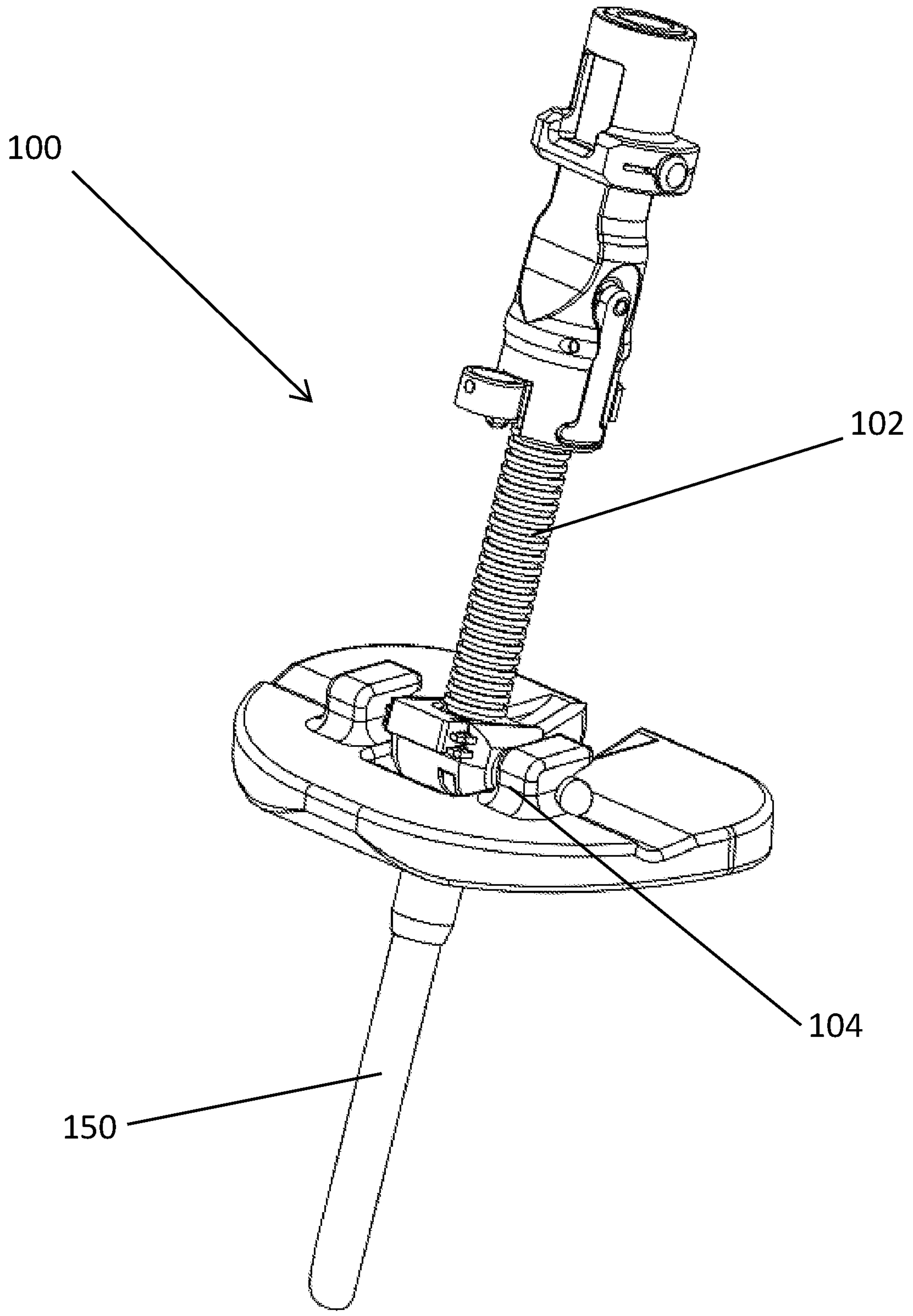
FIG. 1 is a perspective view of a surgical portal device in accordance with certain embodiments of the invention.

While the invention is amenable to various modifications and alternative forms, specifics thereof have been shown by way of example in the drawings and will be described in detail. It should be understood, however, that the intention is not to limit the invention to the particular example embodiments described. On the contrary, the invention is to cover all modifications, equivalents, and alternatives falling within the spirit and scope of the invention as defined by the appended claims. For illustrative purposes, cross-hatching, dashing or shading in the figures is provided to demonstrate sealed portions and/or integrated regions or devices for the package.

DETAILED DESCRIPTION

In the following descriptions, the present invention will be explained with reference to example embodiments thereof. However, these embodiments are not intended to limit the present invention to any specific example, embodiment, environment, applications or particular implementations described in these embodiments. Therefore, description of these embodiments is only for purpose of illustration rather than to limit the present invention. It should be appreciated that, in the following embodiments and the attached drawings, dimensional relationships among individual elements in the attached drawings are illustrated only for ease of understanding, but not to limit the actual scale unless specifically claimed as such.

Figure 2:
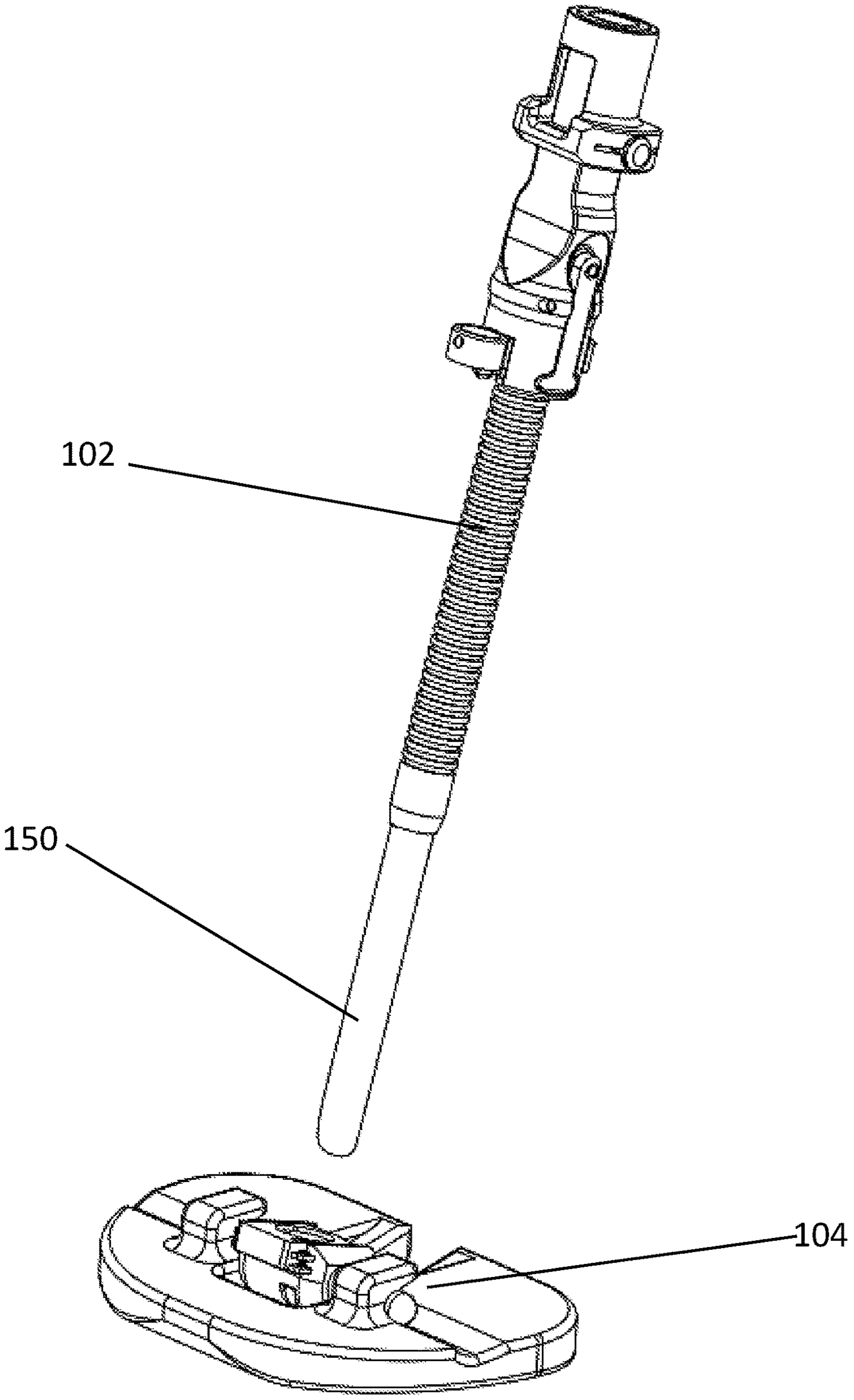
FIG. 2 is another perspective view of a surgical portal device in accordance with certain embodiments of the invention.
Figure 3:
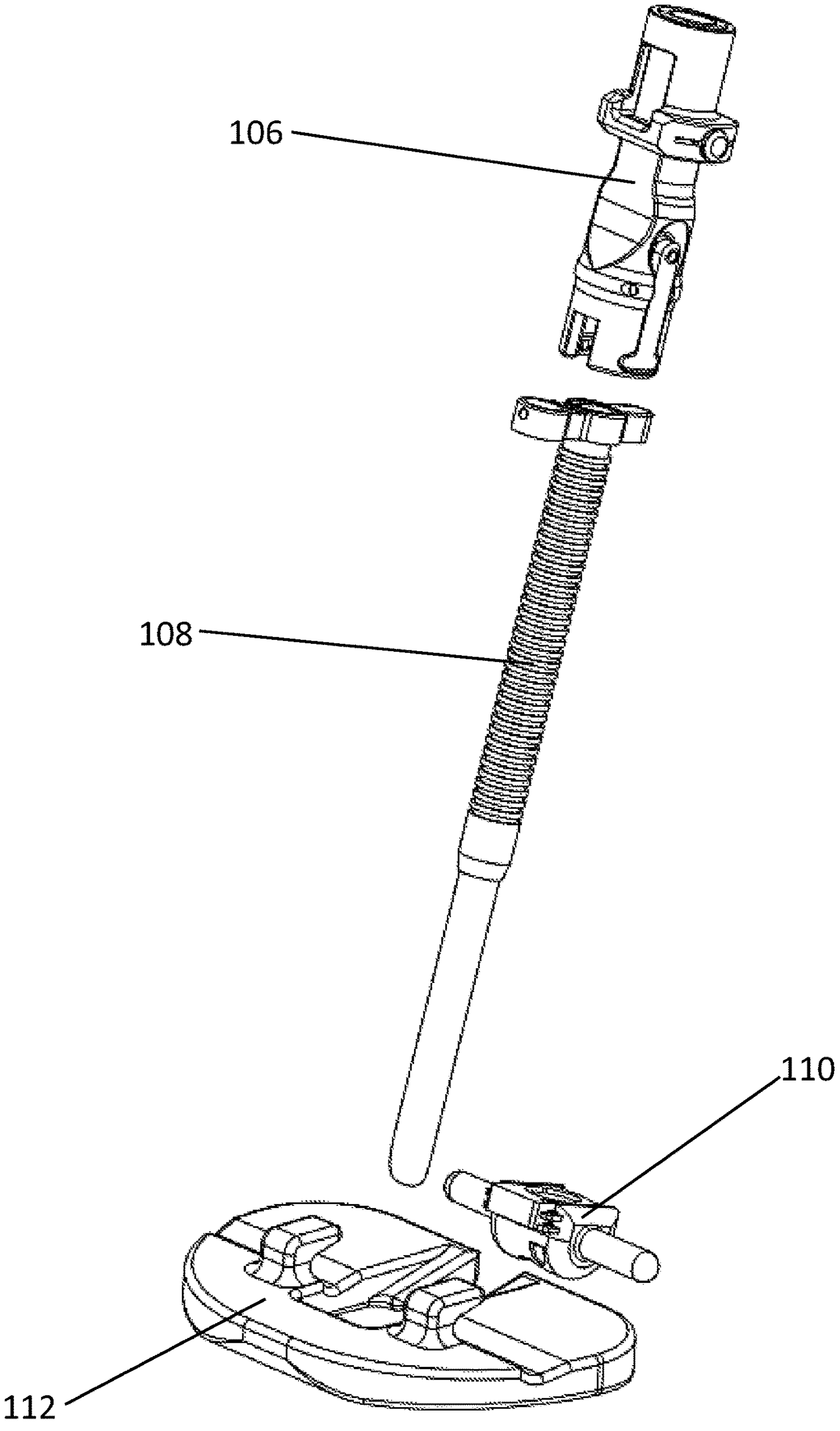
FIG. 3 is a further perspective view of a surgical portal device in accordance with certain embodiments of the invention.
Figure 4:
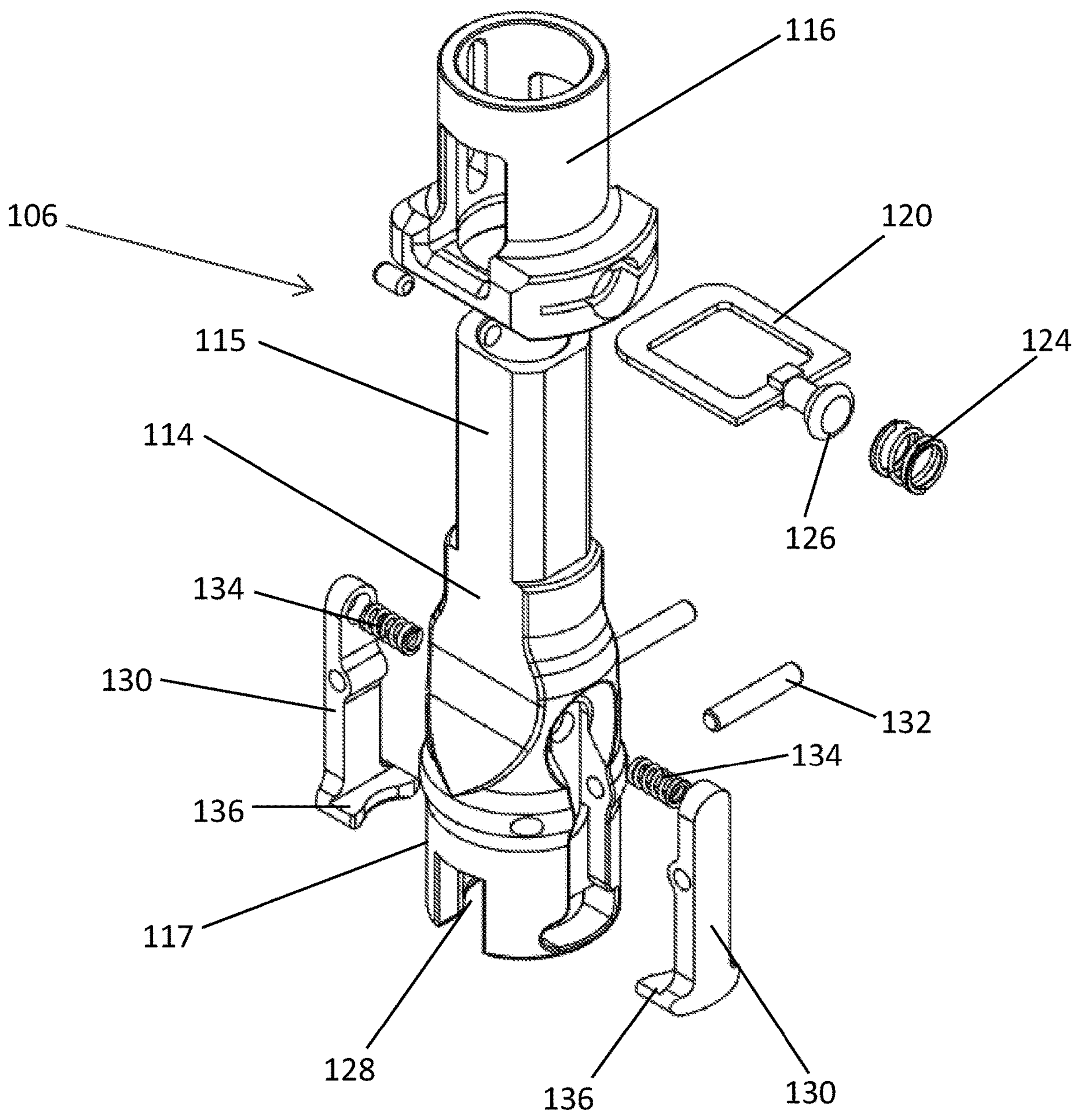
FIG. 4 is a perspective view of a portal head for a surgical portal device in accordance with certain embodiments of the invention.
Figure 5:
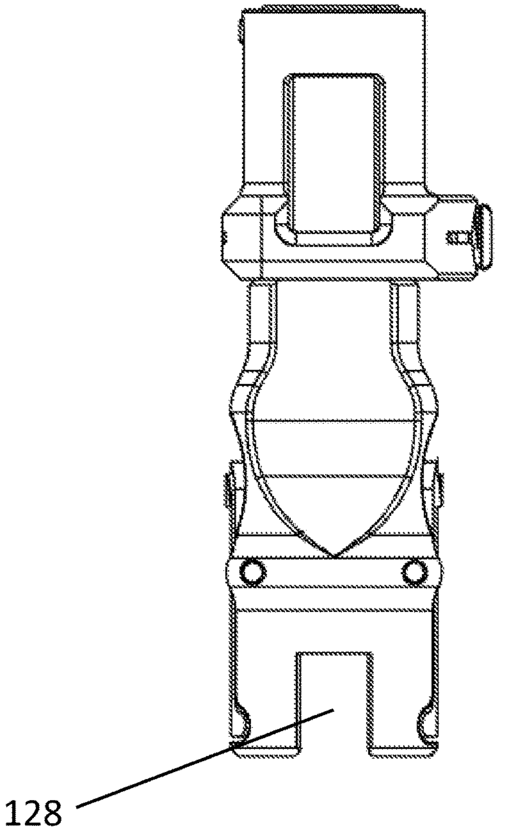
FIG. 5 is a front view of a portal head for a surgical portal device in accordance with certain embodiments of the invention.
Figure 6:
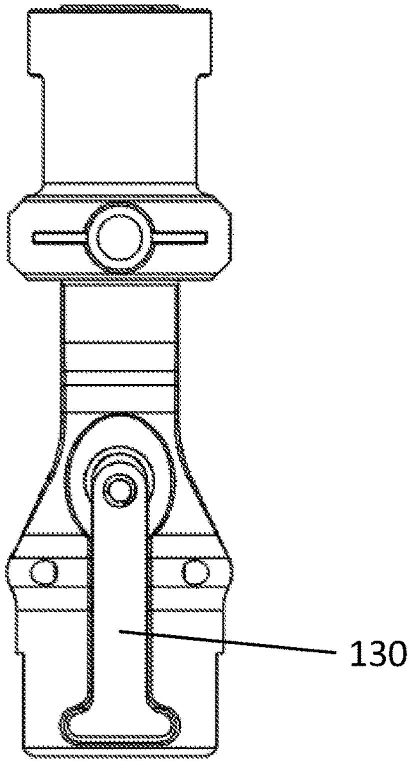
FIG. 6 is a side view of a portal head for a surgical portal device in accordance with certain embodiments of the invention.
Figure 7:
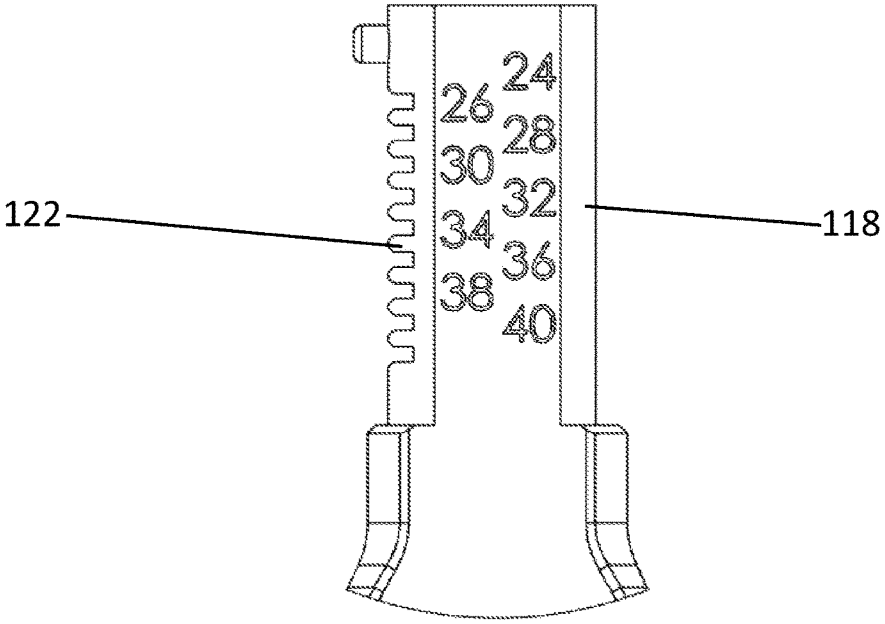
FIG. 7 is a side view of a portion of a portal head for a surgical portal device in accordance with certain embodiments of the invention.
Figure 8:
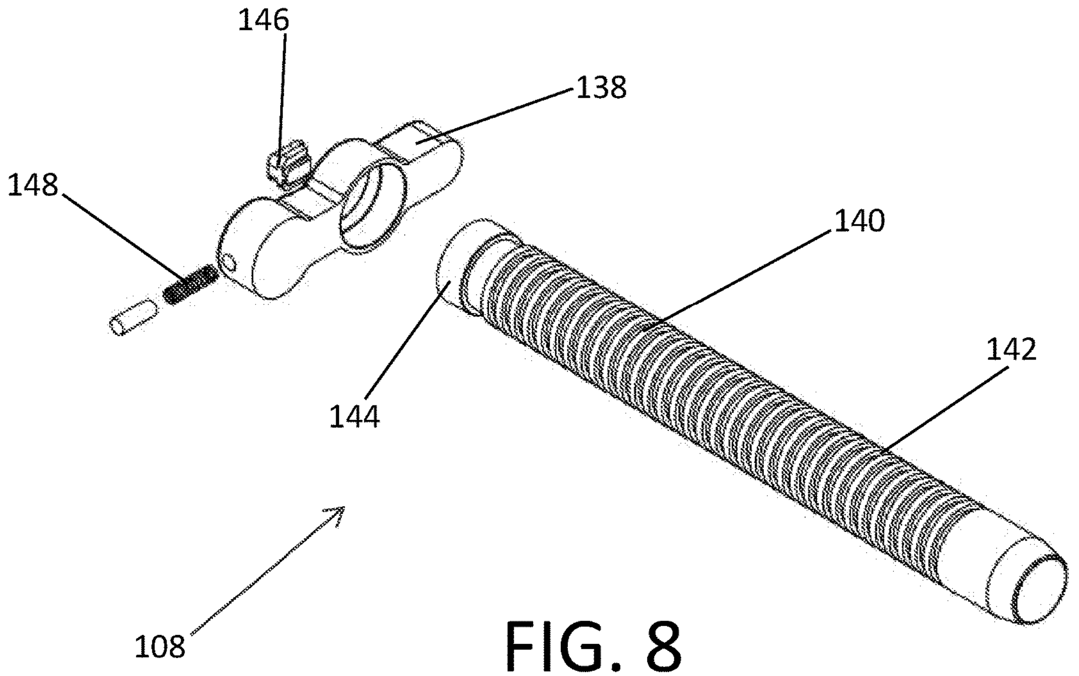
FIG. 8 is an exploded perspective view of a portal tube assembly for a surgical portal device in accordance with certain embodiments of the invention.
Figure 9:
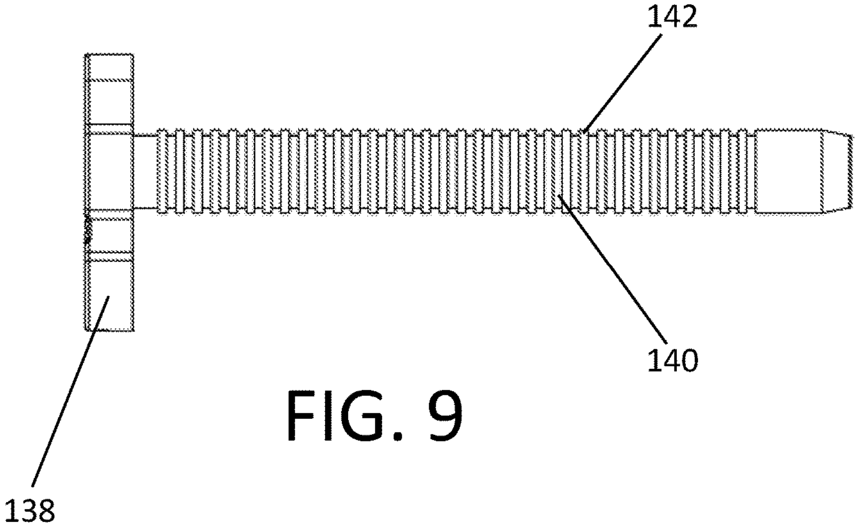
FIG. 9 is a side view of a portal tube assembly for a surgical portal device in accordance with certain embodiments of the invention.
Figure 10:
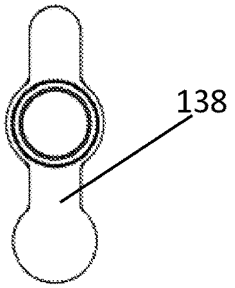
FIG. 10 is an end view of a portal tube assembly for a surgical portal device in accordance with certain embodiments of the invention.
Figure 11:
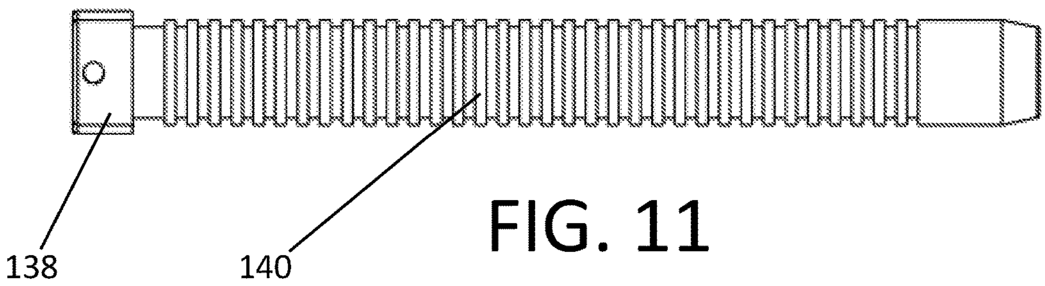
FIG. 11 is a side view of an adjustable stem of a portal tube assembly for a surgical portal device in accordance with certain embodiments of the invention.
Figure 12:
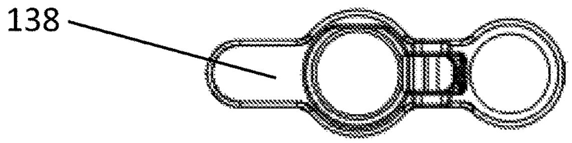
FIG. 12 is a perspective view of a slide lock of a portal tube assembly for a surgical portal device in accordance with certain embodiments of the invention.

Referring to FIGS. 1-3, a surgical portal system 100 is shown. The surgical portal system 100 generally comprises a portal assembly 102 and a base plate assembly 104. The portal assembly 102 comprises a portal head 106 and a portal stem 108 disposed on a distal end of the portal head 106. The base plate assembly 104 comprises a depth stop 110 disposed on a force dissipating plate 112.

Referring to FIGS. 4-7, the portal head 106 is shown. The portal head 106 comprises an elongated hollow base 114 and a longitudinally movable collar 116. The collar 116 slides longitudinally along the upper portion 115 of the base 114 to allow the portal head 106 to be made longer or shorter as desired by the user. A series of markings 118 are defined in or provided to the upper portion 115 to indicate a length dimension for the portal tube, which can adjust depth of instruments placed through the portal.

The length setting of the portal head 106 is securely maintained via a lockout clip 120 provided to the collar 116. The lockout clip is hoop-shaped so that it fits around the upper portion 115 of the base 114. The clip 120 slides laterally (i.e. perpendicular to the longitudinal axis of the base 114 and length adjustment direction) within the collar 116 to engage and disengage a plurality of teeth 122 defined on the upper portion 115 of the base 114. The clip 120 is normally biased with a spring 124 into the engaged or locked position. The user pushes a release button or projection 126 of the clip 120 to overcome the bias force and disengage the clip 120 from the teeth 122 in order to adjust the length of the portal.

A lower portion 117 of the base 114 defines a channel 128 for engaging the portal stem 108. A pair of locking legs 130 are provided to secure the portal stem 108 to the lower portion 117 when the two components are mated together. Each leg 130 pivots about a pin 132 located between longitudinal ends of the leg. An upper end is biased laterally outward via a spring 134, which causes the foot 136 on the opposite longitudinal end to be biased laterally inward to lock the portal stem 108 in the mated position.

Referring now to FIGS. 8-12, the portal stem 108 is shown. The portal stem 108 comprises a locking member 138 that locks onto a proximal or first end of a hollow tubular base member 140. The base member 140 is an elongated hollow tube with a plurality of circumferential ribs 142 defined on its outer surface. A proximal end of the base member 140 defines a flange 144 that facilitates securing to the locking member 138. The distal end of the base member 140 is beveled.

The locking member 138 comprises a laterally-elongated body with an aperture defined through the body in a direction parallel to the longitudinal axis of the base member 140. An engagement member 146 is provided to the locking member 138 to selectively engage the flange 144 of the base member 140 when the locking member is mated with the proximal end of the base member 140. A resilient member, such as a spring 148 is provided in the locking member to bias the engagement member 146 towards the closed or secured state. The user thus must apply sufficient force to the engagement member 146 to overcome the bias force in order to remove the base member 140 from the locking member 138.

Figure 13:
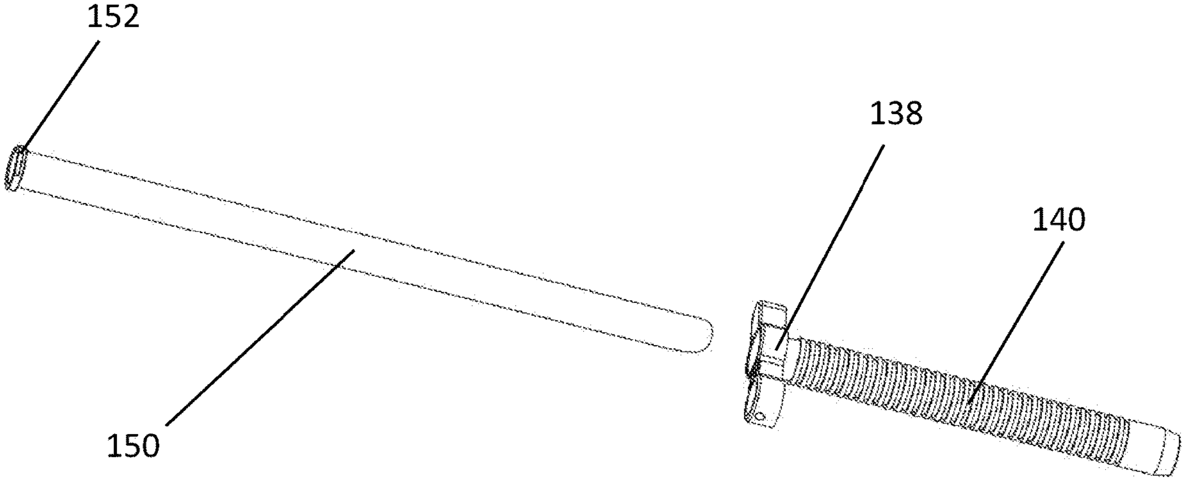
FIG. 13 is a perspective view of a portal tube assembly for a surgical portal device in accordance with certain embodiments of the invention.
Figure 14:
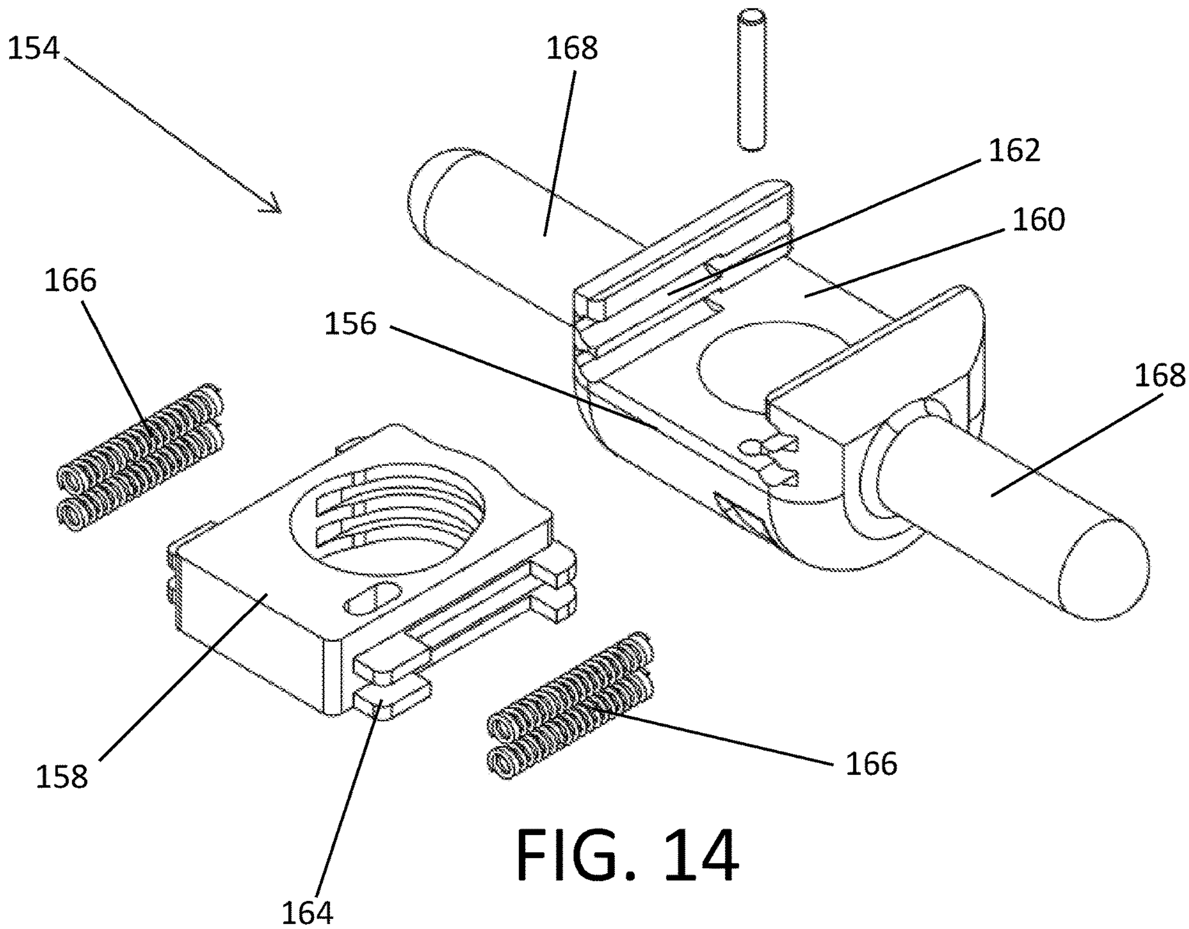
FIG. 14 is a perspective exploded view of a depth stop for a surgical portal device in accordance with certain embodiments of the invention.
Figure 15:
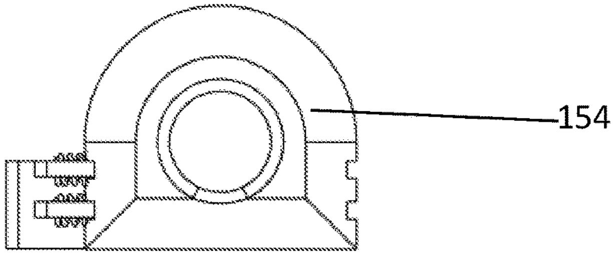
FIG. 15 is a side view of a depth stop for a surgical portal device in accordance with certain embodiments of the invention.
Figure 16:
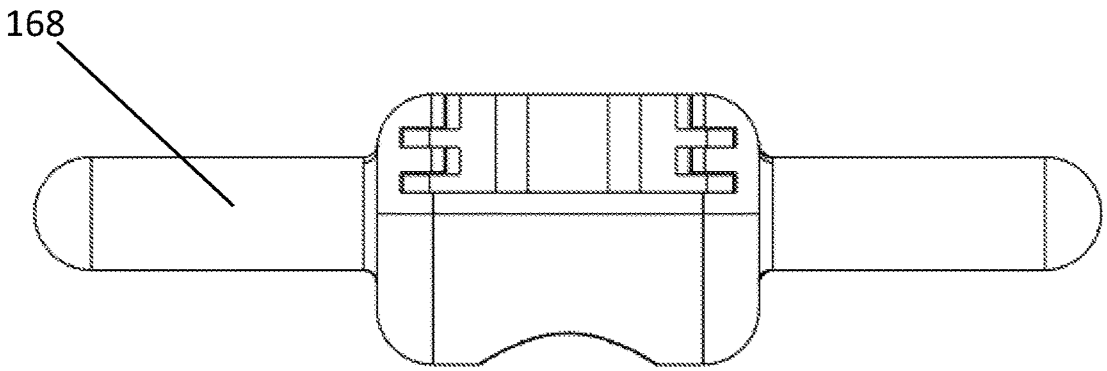
FIG. 16 is a front view of a depth stop for a surgical portal device in accordance with certain embodiments of the invention.
Figure 17:
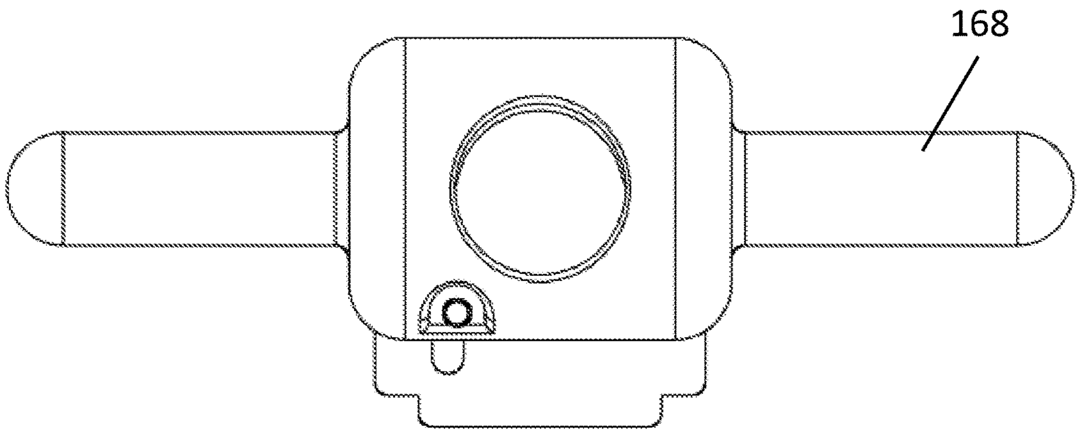
FIG. 17 is a top view of a depth stop for a surgical portal device in accordance with certain embodiments of the invention.
Figure 18:
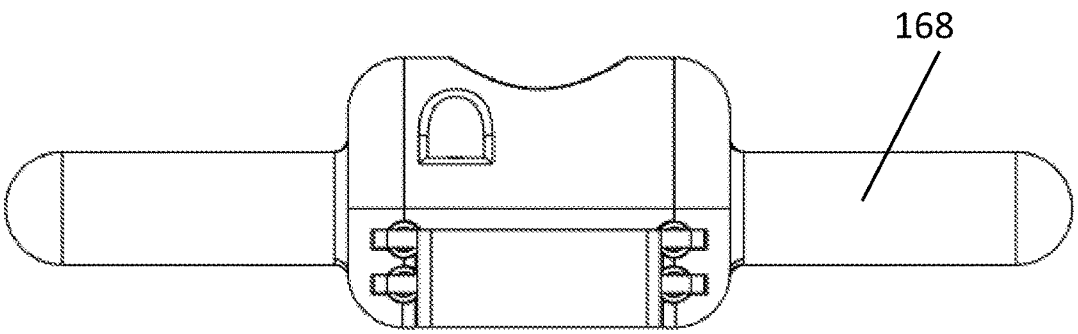
FIG. 18 is a rear view of a depth stop for a surgical portal device in accordance with certain embodiments of the invention.
Figure 19:
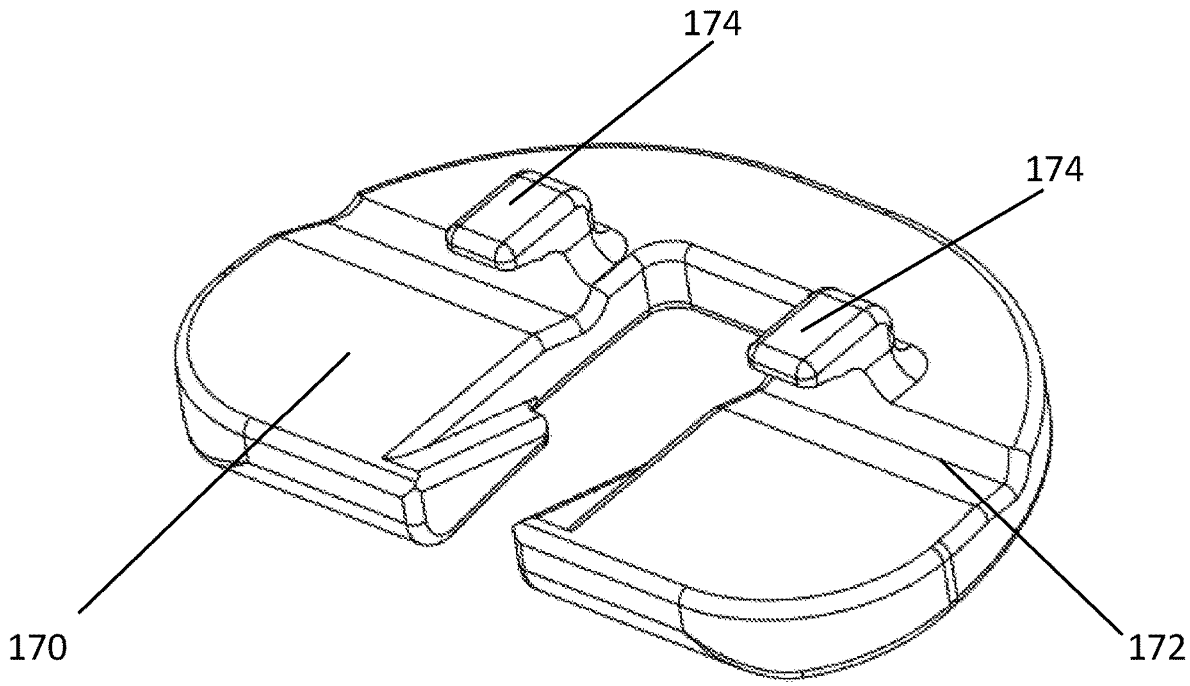
FIG. 19 is a perspective view of a force dissipation plate for a surgical portal device in accordance with certain embodiments of the invention.
Figure 20:
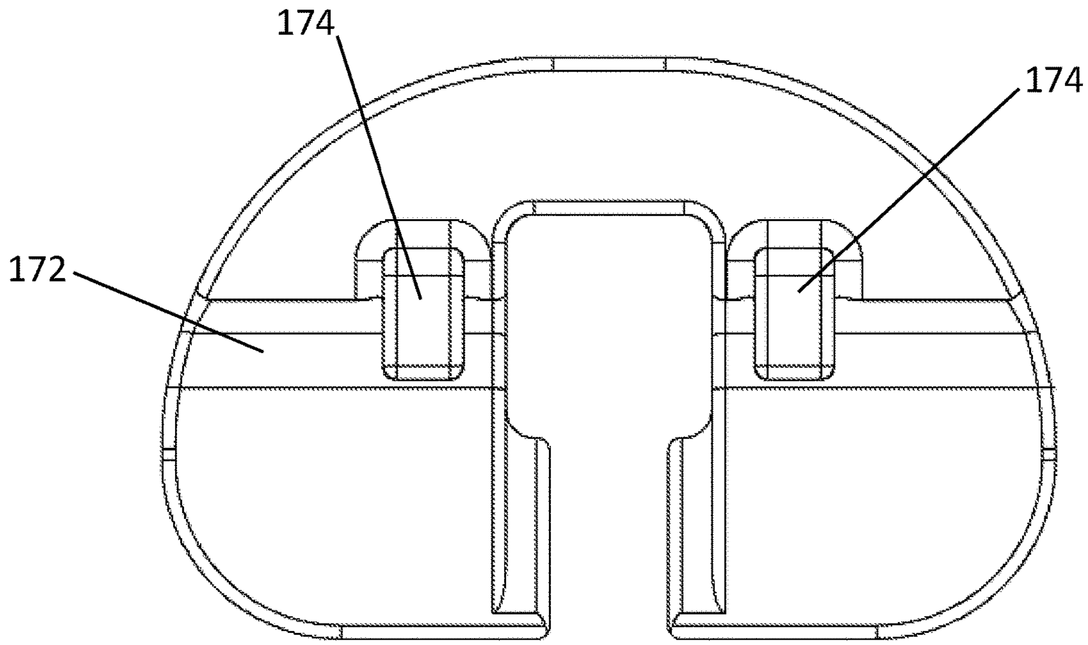
FIG. 20 is a top view of a force dissipation plate for a surgical portal device in accordance with certain embodiments of the invention.
Figure 21:
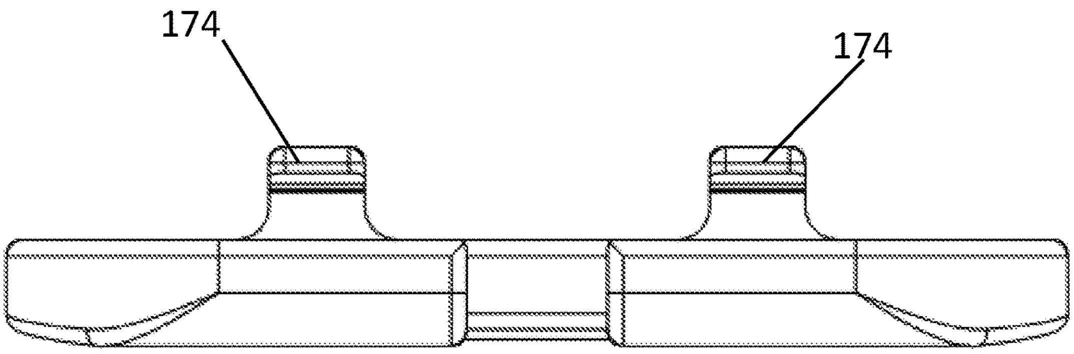
FIG. 21 is a front view of a force dissipation plate for a surgical portal device in accordance with certain embodiments of the invention.
Figure 22:
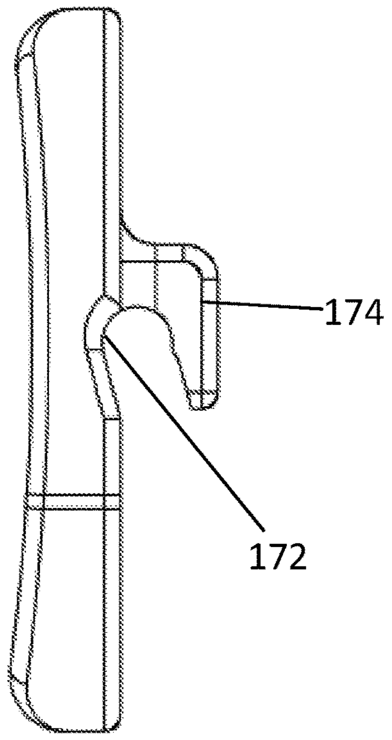
FIG. 22 is a side view of a force dissipation plate for a surgical portal device in accordance with certain embodiments of the invention.

FIG. 13 illustrates a cannula or surgical tube 150 oriented prior to insertion into the inner diameter of the portal stem 108. A flange 152 at the top or proximal end of the tube 150 keeps the tube from passing distally through the portal stem 108. The tube 150 can be mated with the portal stem 108 prior to mating the portal stem 108 with the portal head 106.

Referring now to FIGS. 14-18, the depth stop 154 of the base plate assembly 104 is shown. The depth stop comprises a stop body 156 and a stop release member 158 that slides relative to the stop body 156. Both of the stop body 156 and stop release member have apertures defined therethrough. A channel 160 on a top or proximal side of the stop body 156 is defined for slidably receiving the stop release member 158. Respective grooves 162 in the channel walls and projections 164 on the sides of the stop release member 158 constrain the movement of the stop release member 158 to be perpendicular to the longitudinal axis of the portal stem 108.

Moreover, engagement grooves are defined in the sidewalls of the aperture of the stop release member 158 in order to engage the circumferential ribs 142 of the tubular base member 140. Bias members such as springs 166 are provided to the depth stop 154 to cause the stop release member 158 to be normally biased in the rib engagement state. Thus, users must apply sufficient force to the outer side of the stop release member 158 to release the portal stem 108 from the depth stop for depth adjustment or removal of the portal stem.

The depth stop 154 further comprises a pair of axles 168 that extend horizontally from the stop body 156. The axles are configured to be engaged by the force dissipation plate 170 to restrain vertical movement with respect to the patient, while allowing for pivotal movement relative to the force dissipation plate 170. The curved distal side of the stop body 156 further provides clearance to permit the pivoting movement.

The force dissipation plate 170 is shown in FIGS. 19-22. The force dissipation plate 170 defines a generally planar distal side that contacts the patient. The surface of plate 170 distributes any distally-directed forces (i.e. towards the patient) across the distal surface of the plate so that such forces are lessened at any point towards the patient, thus improving patient safety. Force dissipation devices are further discussed in U.S. Patent App. Pub. No. US 2010/0331882 A1, which is incorporated herein in its entirety as part of this application.

The proximal or top side of the force dissipation plate 170 defines a horizontal groove 172 and a pair of fingers 174 that extend upwards from the proximal surface. The fingers and groove are sized and arranged to allow the axles 168 of the depth stop 154 to be inserted in the groove 172 and secured there against forces in the proximal-distal direction. However, the depth stop 154 is permitted to rotate about the axles 168 as discussed above.

The plurality of circumferential ribs 142 of the portal stem 108 and depth stop 154 allow for rapid depth adjustments. The length of the portal head can also be quickly and easily adjusted to accommodate different length instruments and adjust for instrument depth. In certain embodiments, the components are dimensioned such that there is provided a minimum of six inches of working distance/depth for the portal.

The many surgical portal device adjustments disclosed herein together provide a large range of motion or degrees of freedom for the scope/user position within the constraints of the patient's anatomy. Additional advantages and features of certain embodiments include the ability to quickly switch from surgical instruments to an endoscope and back, the ability to orient a portal tube with the scope beveled tip, and the force dissipation plate allowing for 360 degree rotation of a scope while secured to the force dissipation plate by the depth stop.

The present invention may be embodied in other specific forms without departing from the spirit or essential attributes thereof, and it is, therefore, desired that the present embodiment be considered in all respects as illustrative and not restrictive. Those skilled in the art may recognize other equivalents to the specific embodiment described herein which equivalents are intended to be encompassed by the claims attached hereto.

What is claimed is:

1. A surgical portal, comprising:
- a portal assembly, comprising a portal head and a portal stem disposed on a distal end of the portal head; and
- a base plate assembly, comprising a depth stop disposed on a force dissipating plate;
- wherein the portal head comprises an elongated hollow base and collar, and wherein the collar is configured to slide longitudinally along an upper portion of the elongated hollow base;
- wherein the portal head further comprises a lockout clip provided to the collar such that the lockout clip can slide perpendicular to a longitudinal axis of the elongated hollow base, and wherein the upper portion of the elongated hollow base includes a plurality of teeth that are arranged to be engaged by the lockout clip in a secured state.

2. The surgical portal of claim 1, wherein the portal head further includes a bias member that is arranged to bias the lockout clip in the secured state.

3. The surgical portal of claim 1, wherein a lower portion of the elongated hollow base defines a channel to engage a proximal end of the portal stem.

4. The surgical portal of claim 3, wherein the elongated hollow base comprises a locking leg to secure the portal stem to the lower portion when the proximal end of the portal stem is disposed in the channel, the locking leg pivotally mounted on the lower portion that is biased via a spring to an engaged position.

5. The surgical portal of claim 1, further comprising a surgical tube disposed within the portal stem.

6. The surgical portal of claim 1, wherein the force dissipation plate comprises a plate body including a distal patient-contacting side and a proximal side, the proximal side includes a groove and a pair of fingers that extend upwards from the proximal surface, such that an axle-shaped object in the groove is restrained from movement in a proximal-distal direction while permitting rotation of the axle-shaped object relative to the plate body.

7. A surgical portal, comprising:
- a portal assembly, comprising a portal head and a portal stem disposed on a distal end of the portal head; and
- a base plate assembly, comprising a depth stop disposed on a force dissipating plate;
- wherein the depth stop comprises a stop body and a stop release member that slides relative to the stop body, wherein both of the stop body and stop release member have apertures defined therethrough, and wherein the stop release member includes a channel on a proximal side of the stop body to slidably receive the stop release member.

8. The surgical portal of claim 7, wherein the stop release member includes grooves defined in one or more walls of the channel to engage respective projections defined on one or more sides of the stop release member to constrain the movement of the stop release member in a plane perpendicular to a longitudinal axis of the portal stem.

9. The surgical portal of claim 7, wherein one or more engagement grooves are defined in one or more sidewalls of the aperture defined through the stop release member in order to engage one or more corresponding ribs on an outer surface of the tubular base member.

10. The surgical portal of claim 7, wherein the depth stop further comprises one or more bias members to bias the stop release member in an engagement state.

11. The surgical portal of claim 7, wherein the depth stop further comprises a pair of axles that extend horizontally from the stop body in opposite directions.

12. The surgical portal of claim 7, wherein a distal side of the stop body is curved.

* * * * *